United States Patent [19]
Young

[11] Patent Number: 4,607,221
[45] Date of Patent: Aug. 19, 1986

[54] NUCLEAR MAGNETIC RESONANCE METHOD AND APPARATUS

[75] Inventor: Ian R. Young, Sunbury-on-Thames, England

[73] Assignee: Picker International Limited, Wembley, England

[21] Appl. No.: 533,381

[22] Filed: Sep. 16, 1983

[30] Foreign Application Priority Data

Sep. 17, 1982 [GB] United Kingdom ............... 8226539

[51] Int. Cl.⁴ .......................................... G01R 33/20
[52] U.S. Cl. .................................. 324/306; 324/309
[58] Field of Search ................ 324/300, 306, 309, 311

[56] References Cited

U.S. PATENT DOCUMENTS 3,932,805  1/1976  Abe et al. .......................... 324/309
4,475,084 10/1984  Moore ................................ 324/309
4,520,828  6/1985  Burl et al. .......................... 324/306

FOREIGN PATENT DOCUMENTS 0082684 12/1982 European Pat. Off. .
1578910  5/1978 United Kingdom .
2056088  8/1980 United Kingdom .
2056078  3/1981 United Kingdom .

Primary Examiner—Michael J. Tokar
Attorney, Agent, or Firm—Watts, Hoffmann, Fisher & Heinke Co.

[57] ABSTRACT

A method and apparatus for determining the rate and direction of flow of a liquid in a selected region of a body by NMR techniques. NMR is excited preferentially in a slice of the body which includes the region and then a magnetic field having a gradient in a direction parallel to the flow of the liquid is applied, this field being effective to cause a phase difference between the resonance for the liquid which is flowing, or has flowed, in the region and the resonance for the rest of the slice. The free induction decay signal is measured, and the phase difference between the signal from the liquid, and the signal from the rest of the slice is related to the rate of flow of the liquid through the region.

8 Claims, 3 Drawing Figures

NUCLEAR MAGNETIC RESONANCE METHOD AND APPARATUS

This invention relates to methods and apparatus for determining the rate of flow of a liquid in a selected region of a body by nuclear magnetic resonance (NMR) techniques.

NMR techniques have been used for the chemical analysis of material for many years. More recently NMR techniques have been used to obtain images representing the distribution over a selected cross-sectional slice or volume of a body of a chosen quantity, e.g. the density of chosen nuclei, for example hydrogen protons, or of NMR spin relaxation time constants. Such distributions are similar to, although of different significance from, the distribution of X-ray attenuation provided by computerised tomography systems. In some applications it would be useful to obtain additional information relating to the flow rates of a liquid within a selected region of the body, e.g. blood flow in selected veins and arteries of a human body, using NMR techniques.

It is an object of the invention to provide a method of determining the rate of flow of a liquid in a selected region of a body by NMR techniques and an apparatus arranged to perform such a method.

According to the present invention a method of determining the rate of flow of a liquid containing a selected nuclei in a selected region of a body comprises: exciting nuclear magnetic resonance for said nuclei preferentially in a slice of said body which includes said region; subsequently applying a magnetic field having a gradient in a direction parallel to the flow of said liquid which is effective to cause a phase difference between the resonance for the liquid which is flowing, or has flowed, in said region and the resonance for the rest of said slice; measuring the free induction decay signal; and relating the phase difference between the signal from said liquid and the signal from said rest of said slice to the rate of flow of said liquid through said region.

In one particular method in accordance with the invention said slice is preferentially excited by applying a first magnetic field having a gradient in a direction parallel to the flow of said liquid together with an RF pulse, and said subsequent magnetic field has a magnitude sufficient to cause the resonance for said rest of said slice to rephase.

The invention also provides an apparatus arranged to carry out a method according to the invention, said apparatus comprising: means arranged to excite nuclear magnetic resonance for said nuclei preferentially in a slice of said body which includes said region; means arranged to subsequently apply a magnetic field having a gradient in a direction parallel to the flow of said liquid; means arranged to measure the free induction decay signal; and means arranged to relate the phase difference between the signal from said liquid and the signal from the rest of said slice to the rate of flow of said liquid through said region.

One method and apparatus in accordance with the invention will now be described, by way of example only with reference to the accompanying drawings in which.

The method is performed using an apparatus essentially identical to that described in U.K. Patent Specification Nos. 1,578,910 or 2,056,078, to which reference should be made for a fuller description, appropriately programmed to apply a sequence of magnetic field gradient and RF pulses and analyse the resulting signals as hereafter described.

The essential features of such an apparatus in so far as is required for an understanding of the present invention are as follows:

The apparatus includes a first coil system whereby a magnetic field can be applied to a body to be examined in a given direction, normally designated the Z-direction, with a gradient in any one or more of the three orthogonal directions i.e. X, Y and Z directions.

Figure 1:
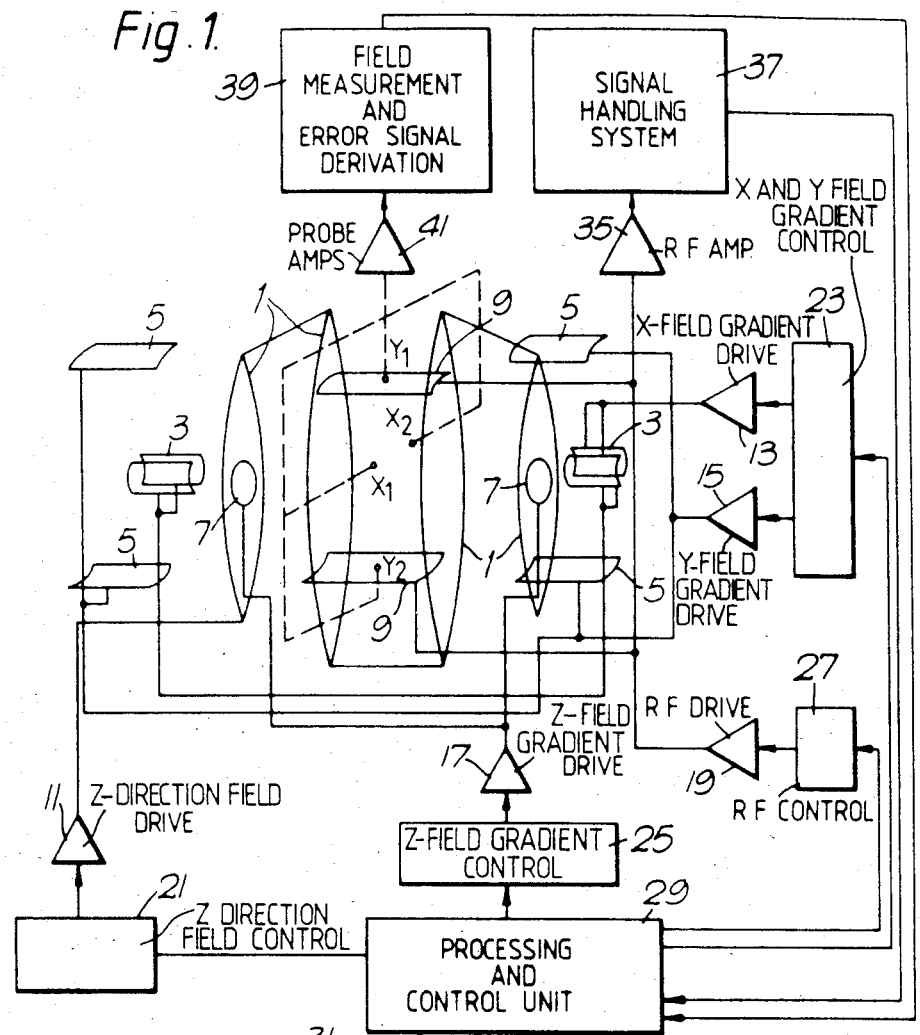
FIGS. 1 and 2 illustrate the apparatus diagramatically.

Referring to FIG. 1, the first coil system comprises coils 1 capable of providing a steady uniform magnetic field in the Z direction; coils 3 capable of provising a magnetic field gradient in the X direction, coils 5 capable of providing a magnetic field gradient in the Y direction; and coils 7 capable of providing a magnetic field gradient in the Z direction.

In addition, the apparatus includes a second coil system 9 whereby RF magnetic fields can be applied to the body under examination in a plane normal to the direction of the steady uniform magnetic field produced by the first coil system, and whereby RF magnetic fields resulting from nuclei in the body under examination which have been excited to nuclear magnetic resonance with a spin vector component other than in the Z direction can be detected.

In the drawing a single pair of coils 9 is shown for both applying and detecting RF fields, but in certain circumstances it may be preferable to provide separate coils for detecting the RF fields.

The various coils 1, 3, 5, 7 and 9 are driven by drive amplifiers 11, 12, 13, 15, 17 and 19 respectively, controlled by control circuits 21, 23, 25 and 27 respectively. These circuits may take various forms which are well known to those with experience of NMR equipment and other apparatus using coil induced magnetic fields.

The circuits 21, 23, 25 and 27 are controlled by a central processing and control unit 29 with which are associated inputs and other peripherals 31, for the provision of commands and instructions to the apparatus, and a display 33.

The NMR signals detected by the coils 9 are applied via an amplifier 35 to a signal handling system 37. The signal handling system is arranged to make any appropriate calibration and correction of the signals, but essentially transmits the signals to the processing and control unit 29 wherein the signals are processed for application to the display to produce an image representing the distribution of an NMR quantity in the body being examiner.

It will be appreciated that whilst shown separately to clarify the present description, the signal handling system 37 may conveniently form part of the unit 29.

Figure 2:
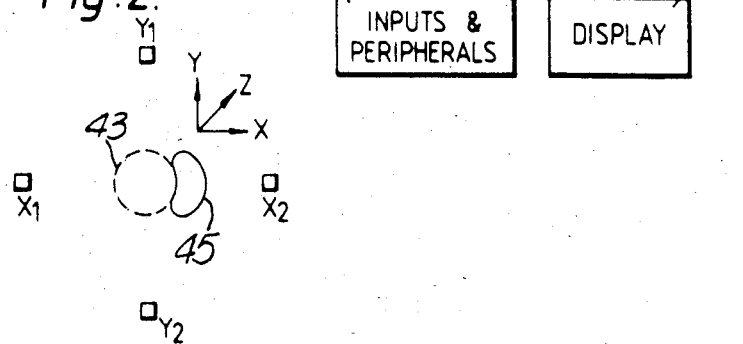

The apparatus also includes field measurement and error signal circuits 39 which receive signals via amplifiers 41 from fields probes $X_1$, $X_2$, $Y_1$, and $Y_2$ which are disposed at suitable positions in relation to a slice 43 named to the Z direction of the body to be examined, as illustrated in FIG. 2, to monitor the applied magnetic fields.

For reasons explained hereafter an enclosure 45 containing a volume of water is placed adjacent the body, the enclosure being positioned so that the water lies in the plane of the slice 43.

Figure 3:
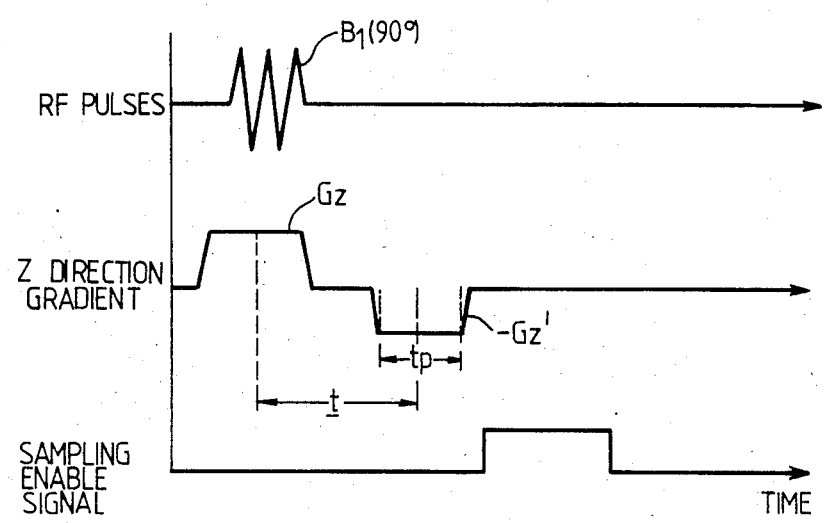
FIG. 3 illustrates the magnetic field sequence employed in the method.

Referring now also to FIG. 3, in operation of the apparatus a steady uniform magnetic field Bo is applied to the body under examination in the Z direction by the first coil system 1. This field serves to define the equilibrium axis of magnetic alignment of the nuclei in the body, i.e. along the positive Z direction, and remains constant throughout the examination procedure. An additional magnetic field Gz having a magnetic field gradient along the Z direction is then applied to the body, together with an RF magnetic field pulse denoted $B_1$ (90°). The frequency of the RF field is chosen to be the Larmor frequency for hydrogen nuclei, i.e. protons in the slice 43 of the body such that protons within the slice are preferentially excited, the slice consisting of an area of substantially solid material through which a series of blood vessels extend, the protons within the volume of water in the enclosure 45 also being excited. The integral of the RF pulse is such that the pulse is just sufficient to tip the spins of the excited protons into the X-Y plane, and is thus referred to as a 90° pulse, the spins then precessing in the X-Y plane round the Z axis.

The gradient field Gz is then removed, and replaced by a magnetic field $-Gz'$ having a gradient in the opposite sense. This causes the rephasing of the spins which have been selectively excited by the combination of the RF pulse $B_1$ (90°), Bo and the gradient field Gz, the dephasing having been caused by the gradient through the slice. The magnitude of $-Gz'$ is adjusted so that the spins are rephased at the time at which this gradient is switched off as described, for example in the above mentioned UK Patent Specification No. 1,578,910. The excited spins from the blood within the slice having a component of flow along the Z direction will, however, in the time between the application of the gradient fields Gz and $-Gz'$ have moved within the slice, or out of the slice, by an amount dependent on the flow rate of the blood through the slice. Thus the rephasing gradient field $-Gz'$ will be effective to cause a phase difference in the precession in the X-Y plane about the Z axis of the spins from the flowing blood within the slice, and the spins from the substantially static material, i.e. within the slice 43 and in the enclosure 45, the sense of this phase difference being related to the direction of flow relative to the direction of the rephasing gradient on the gradient field $-Gz'$.

The signal induced in the second coil system by the spins precessing in the X-Y plane, i.e. the Free Induction Decay (F.I.D.) signal is then recorded. This will be a composite signal consisting of a contribution from the static material within the slice and enclosure, and a phase shifted contribution from the blood flowing through the slice, the magnitude of the phase shift, $\phi$ being given by the expression:

$$\phi = 2\pi\gamma |-Gz'| \nu t \, tp$$

where $\gamma$ is the Larmor constant for hydrogen protons;

$|-Gz'|$ is the amplitude of the rephasing gradient field $-Gz'$, $\nu$ is the flow velocity of the blood through the slice;

t is the time between the application of the gradient fields Gz and $-Gz'$; and tp is the effective duration of the rephasing gradient field $-Gz'$.

As part of the signal from the static material is derived from the water contained within the enclosure 45 the signal from this static water can be used as a reference signal from which the phase shift $\phi$ can be measured. If the volume of water and thus the spin density of protons within the enclosure, and the spin-lattice relaxation time $T_1$ for the protons within the water are known quantities, by taking a series of measurements with different values of the time period t between the application of the gradient fields enough data can be obtained to enable other variables e.g. proton density and the relaxation time constants $T_1$ and $T_2$ to be established.

It will be appreciated that this method of measuring flow rates is particularly convenient for the measurement of fast flow rates. The method can be adapted to the measurement of relatively slow flow rates, however, by the choice of longer values of the time period t.

It will also be appreciated that whilst the method described hereinbefore relates to determining the rate of flow of a liquid which contains hydrogen nuclei, the method is equally applicable to determining the rate of flow of a liquid containing other nuclei having a magnetic spin, e.g. $^{31}P$, by appropriate choice of the RF pulse frequency.

I claim:

1. A method of determining the rate of flow along a predetermined direction of a liquid containing a selected nuclei in a selected region of a body comprising: exciting nuclear magnetic resonance for said nuclei preferentially in a slice of said body which includes said region; subsequently applying a magnetic field having a gradient along said predetermined direction which is effective to cause a phase difference between the resonance for the liquid which is flowing, or has flowed in said predetermined direction, in said region and the resonance for the rest of said slice; measuring the free induction decay signal so as to obtain a measurement representative of said phase difference; and relating said phase difference to the rate of flow along said predetermined direction of said liquid through said region.

2. A method according to claim 1 in which said slice is preferentially excited by applying a first magnetic field having a gradient along said predetermined direction together with an RF pulse, and said subsequent magnetic field has a magnitude sufficient to cause the resonance for said rest of said slice to rephase.

3. A method according to claim 1 in which a volume of a material containing said nuclei having known nuclear magnetic resonance properties is excited together with said slice to act as a source of a reference signal of phase corresponding to said signal from said rest of said slice.

4. A method according to claim 1 in which said relating includes determining the sense of flow along said predetermined direction of said liquid through said region.

5. A sequence including a method according to claim 1 in which said method is repeated with different values of the time period between said exciting and said subsequently applying to enable the determination of quantities relating to nuclear magnetic resonance from said signal.

6. An apparatus arranged to determine the rate of flow along a predetermined direction of a liquid containing a selected nuclei in a selected region of a body comprising: means arranged to excite nuclear magnetic resonance for said nuclei preferentially in a slice of said body which includes said region; means arranged to subsequently apply a magnetic field having a gradient along said predetermined direction; and means arranged to measure the free induction decay signal so as to enable a measurement representative of said phase difference to be obtained; and means arranged to relate said phase difference to the rate of flow of said liquid along said predetermined direction through said region.

7. An apparatus according to claim 6 in which said means arranged to excite comprises means arranged to apply a first magnetic field having a gradient along said predetermined direction, together with an RF pulse, and said means arranged to subsequently apply comprises means for applying a magnetic field which has a magnitude sufficient to cause the resonance for said rest of said slice to rephase.

8. An apparatus according to claim 6 in which a volume of a material containing said nuclei having known magnetic resonance properties is provided adjacent to said slice.

* * * * *